US011766473B2

(12) United States Patent
Popescu et al.

(10) Patent No.: US 11,766,473 B2
(45) Date of Patent: Sep. 26, 2023

(54) THERAPEUTIC CANCER VACCINE CONTAINING TUMOR-ASSOCIATED NEOANTIGENS AND IMMUNOSTIMULANTS IN A DELIVER SYSTEM

(71) Applicant: Xeme Biopharma Inc., Lombard, IL (US)

(72) Inventors: Mircea C. Popescu, Plainsboro, NJ (US); Richard J. Robb, Gaithersburg, MD (US)

(73) Assignee: Xeme Biopharma Inc., Monmouth Junction, NJ (US)

( * ) Notice: Subject to any disclaimer, the term of this patent is extended or adjusted under 35 U.S.C. 154(b) by 460 days.

(21) Appl. No.: 16/881,580

(22) Filed: May 22, 2020

(65) Prior Publication Data

US 2020/0376101 A1 Dec. 3, 2020

Related U.S. Application Data

(63) Continuation of application No. 15/424,473, filed on Feb. 3, 2017, now abandoned.

(60) Provisional application No. 62/292,029, filed on Feb. 5, 2016.

(51) Int. Cl.
| | |
|---|---|
| *C07K 14/00* | (2006.01) |
| *A01N 37/18* | (2006.01) |
| *A61K 39/00* | (2006.01) |
| *C12Q 1/6886* | (2018.01) |

(52) U.S. Cl.
CPC ........ *A61K 39/0011* (2013.01); *C12Q 1/6886* (2013.01); *A61K 2039/55533* (2013.01); *C12Q 2600/106* (2013.01); *C12Q 2600/156* (2013.01)

(58) Field of Classification Search
CPC .......................... A61K 39/0011; C12Q 1/6886
See application file for complete search history.

(56) References Cited

U.S. PATENT DOCUMENTS

| | | |
|---|---|---|
| 6,906,170 B1 | 6/2005 | Lider et al. |
| 2007/0071723 A1 | 3/2007 | Coffey et al. |
| 2010/0226973 A1 | 9/2010 | Fujii et al. |
| 2011/0123438 A1 | 5/2011 | Wickline et al. |
| 2011/0293637 A1 | 12/2011 | Hacohen et al. |
| 2014/0079706 A1 | 3/2014 | Cannarile et al. |
| 2014/0377221 A1 | 12/2014 | Tufaro et al. |
| 2015/0140041 A1 | 5/2015 | Vitiello |
| 2015/0224182 A1 | 8/2015 | Hunt et al. |
| 2016/0008447 A1 | 1/2016 | Hacohen et al. |
| 2016/0058853 A1 | 3/2016 | Sahin et al. |
| 2016/0069895 A1 | 3/2016 | Delamarre et al. |
| 2016/0101170 A1 | 4/2016 | Hacohen et al. |
| 2016/0125129 A1 | 5/2016 | Sahin et al. |
| 2016/0175414 A1 | 6/2016 | Sahin et al. |
| 2016/0186260 A1 | 6/2016 | Klinger et al. |
| 2016/0237163 A1 | 8/2016 | Sariel et al. |
| 2016/0310584 A1 | 10/2016 | Fritsch et al. |
| 2016/0339090 A1 | 11/2016 | Hacohen et al. |

FOREIGN PATENT DOCUMENTS

| | | |
|---|---|---|
| WO | 2014159435 A1 | 10/2014 |
| WO | 2016128060 A1 | 8/2016 |
| WO | 2016128542 A1 | 8/2016 |
| WO | 2016146035 A1 | 9/2016 |
| WO | 2016174085 A1 | 11/2016 |
| WO | 2016187508 A2 | 11/2016 |

OTHER PUBLICATIONS

Hans-Georg Rammensee et al., HLA Ligandome Tumor Antigen Discovery for Personalized Vaccine Approach, Expert Review Vaccines 12(10), pp. 1211-1217 (2013), www.expert-reviews.com.
Gabriela Andrea Pizzurro et al., Dendritic Cell-Based Vaccine Efficacy: Aiming for Hot Spots, Frontiers in Immunology, Mar. 3, 2015, vol. 6, Art. 91, pp. 1-8.
Hans-Georg Rammensee et al., Towards Patient-Specific Tumor Antigen Selection for Vaccination, Immunological Reviews 2002, vol. 188, pp. 164-176, Blackwell Munksgaard 2002, Denmark.
Karrie K. Wong et al., Advances in Therapeutic Cancer Vaccines, Advances in Immunology, vol. 130, pp. 191-249, Elsevier Inc., Jan. 19, 2016, ISSN 0065-2776.
Sofia Farkona et al., Cancer Immunotherapy: the Beginning of the End of Cancer?, BMC Medicine, May 5, 2016, pp. 1-18, Creative Commons.
Bayer AG, American Society of Hematology; Bayer, University of Texas Southwestern, Stellar Clinical Data (Phase I)(non-Hodgkin Lymphoma); R&D Focus Drug News, Jan. 31, 2012, ISSN 1350-1135, IMSworld Publications Ltd.
Shinjiro Sakamoto et al.; Immunological Evaluation of Peptide Vaccination for Cancer Patients with the HLA-A26 Allele; Cancer Science, Oct. 2015, vol. 106, No. 10, pp. 1257-1263, Wiley-Blackwell, Hoboken, NJ.
Lo et al., Anti-GD3 Chimeric sFv-CD28/T-Cell Receptor z Designer T Cells for Treatment of Metastatic Melanoma and Other Neurectodermal Tumors, "Clinical Cancer Research" May 11, 2010, p. 2769-2780.
John et al., Blockade of PD-1 immunosuppression boosts CAR T-cell therapy, "OncoImmunology" Oct. 2013, 3 pages.
Mansour et al. Therapy of established B16-F10 melanoma tumors by a single vaccination of CTL/T helper peptides in VacciMax®, "Journal of Translational Medicine", Apr. 23, 2007, p. 1-8.

(Continued)

*Primary Examiner* — Mark Halvorson
(74) *Attorney, Agent, or Firm* — Banner & Witcoff, Ltd.

(57) ABSTRACT

A therapeutic vaccine and a method of cancer treatment by inducing humoral and cellular immune responses against malignant cells is provided. The vaccine comprises a delivery system that incorporates at least one peptide whose sequence encompasses a genetic mutation associated with a malignancy (neoantigen), at least one immunostimulant, and at least one type of lipid molecule.

8 Claims, 4 Drawing Sheets

Specification includes a Sequence Listing.

(56) References Cited

OTHER PUBLICATIONS

Popescu et al., A Novel Proteoliposomal Vaccine Elicits Potent Antitumor Immunity In Mice, Blood, 109:5407-5410, 2007.
Konigsburg et al., The Development of IL-2 Conjugated Liposomes for Therapeutic Purposes, Biochim Biophys Acta, 1370:243-251, 1998.

Fatty Acid Attachment Element

THERAPEUTIC CANCER VACCINE CONTAINING TUMOR-ASSOCIATED NEOANTIGENS AND IMMUNOSTIMULANTS IN A DELIVER SYSTEM

RELATED APPLICATIONS

This application is a continuation of U.S. application Ser. No. 15/424,473, filed Feb. 3, 2017, which claims priority from U.S. Provisional Patent Application No. 62/292,029, filed Feb. 5, 2016, which is hereby incorporated herein by reference in its entirety for all purposes.

FIELD

The technology described herein relates to the identification of tumor-associated antigens and proteins, and the development of associated peptide vaccines for the therapeutic treatment of cancer. Specifically, this disclosure relates to cancer vaccines engineered from an individual patient's cancer that include natural or modified neoantigens that stimulate the body's humoral and cellular immune responses against the invading cancer cells.

BACKGROUND

Efforts to treat patients with cancer utilizing the immune system dates back to the 1890s. Cancer immunology and immunotherapy has advanced since then, and researchers have gained a better understanding of how the immune system identifies and attempts to destroy cancer cells. Researchers have also gained a better understanding of how cancers can undermine the immune system's ability to identify and destroy the cancer cells and significant progress has been made in the past decade in the treatment of cancer. Targeted forms of chemotherapy and various types of passive and active immunotherapy have improved clinical response rates, delayed disease progression, and prolonged survival.

Nevertheless, additional and less-toxic therapeutic modalities are needed to address the family of cancer diseases. In particular, the individualized genetic make-up of cancer requires a more patient-specific response. Therapeutic vaccination, for example, aims to induce an active immune response to the patient's tumor and is an approach that holds particular promise for specificity and low toxicity, with the potential of long-term disease-free survival by activating the host's anti-tumor immune surveillance. Successful development of cancer vaccines, however, has faced many challenges. For example, one of the main problems is a lack of efficacy due to weak immunogenicity of the vaccine and the difficulty of identifying tumor specific antigens common to all patients within a particular indication. Another important reason for the limited success of therapeutic cancer vaccines has been the lack of recognition that cancer is a heterogeneous genetic disease and that the magnitude of mutations found in a tumor demand an immunologically critical approach to capturing the tumor antigenic diversity in a vaccine. Vaccines made with only one or a few tumor-associated antigens generally have been unsuccessful or marginally successful in clinical studies.

To overcome some of these deficiencies, some vaccine products have utilized whole tumor cells or tumor-cell extracts. Another recent approach is to perform genetic sequencing of biopsy material to identify the full range of genetic mutations (i.e., neoantigens), present in tumor-cell proteins. A subset of the identified genetic mutations or neoantigens is then selected based upon their predicted affinity for binding to the individual patient's Major Histocompatibility Complex (MHC). A typical cancer patient will have 100 to 150 genetic mutations, often consisting of a single amino acid substitution. Of these 20-25 mutations will be encoded within peptide segments that bind well to the patient's particular MHC protein alleles.

MHC proteins on the surface of antigen-presenting cells (APC) bind and present peptide antigens to the helper and effector T cells of the immune system, thus directing an immune response to the tumor. MHC Class I proteins typically present peptides of 8-11 amino acids in length while MHC Class II proteins present peptides of 20-25 amino acids. Such neoantigen peptides can be utilized as the tumor antigen component of a cancer vaccine. Two other approaches that have been used to increase the efficacy of cancer vaccines include the incorporation of tumor antigens into a liposomal particle to enhance uptake by antigen presenting cells, and the use of immunostimulating cytokines, such as interleukin 2 (IL-2) or GM-CSF, to more effectively induce cell-mediated and humoral immunity. See U.S. Pat. No. 6,312,718, Vaccine for B-Cell Malignancies, and U.S. Pat. No. 6,544,549, Multilamellar Coalescence Vesicles (MLCV) Containing Biologically Active Compounds, incorporated herein by reference in their entirety for all purposes.

SUMMARY

This Summary provides an introduction to some general concepts relating to this disclosure in a simplified form that are further described below in the Detailed Description. This Summary is not intended to identify key features or essential features of the disclosure.

Embodiments of the present disclosure are directed to therapeutic cancer vaccines and related methods of treatment that combine neoantigen peptide sequences with immunostimulants in a delivery system designed for efficient uptake by APC and activation of effector immune responses in a cancer patient. Delivery systems can include, for example, liposomes, systems made of cholesterol, cholesterol hemisuccinate or alpha-tochoferol (e.g., vitamin E), or other amphipathic molecules in which modified or synthesized neoantigens can attach or insert. According to one aspect, the therapeutic cancer vaccine includes at least one neoantigen, and the neoantigen includes a tumor-associated genetic mutation peptide. According to another aspect, the tumor-associated genetic mutation peptide is engineered to further include an attachment element. According to one aspect, the attachment element is a transmembrane domain. According to another aspect, the attachment element is a fatty acid linker. According to yet another aspect, the attachment element is a tryptophan attachment element. According to yet another aspect, the attachment element comprises a peptide sequence of 1 to 30 amino acids. According to another aspect, the therapeutic cancer vaccine also includes at least one immunostimulant and at least one type of lipid molecule.

According to another aspect, a method of cancer treatment by inducing humoral and cellular immune responses against cancer cells in a patient is disclosed. According to one aspect, the method requires the genetic sequencing a tumor-tissue sample from a patient to identify a plurality of neoantigens present in the tumor-tissue sample, and wherein the neoantigens include tumor-associated genetic mutation peptides. According to one aspect, at least one neoantigen is selected based upon a predicted affinity for binding to a MHC of the patient, wherein MHC proteins on a surface of antigen-presenting cells of the patient bind and present the neoantigens to helper and effector T cells of an immune system of the patient, and wherein an immune response is directed to the cancer cells in a patient. According to another aspect, a therapeutically effective amount of a vaccine including the neoantigen is administered to the patient, wherein the neoantigen includes a tumor-associated genetic mutation peptide, and wherein the tumor-associated genetic mutation peptide further includes an attachment element selected from the group consisting of a transmembrane domain, a fatty acid linker, and a tryptophan attachment element, wherein the attachment element comprises a peptide sequence of 1 to 30 amino acids; at least one immunostimulant; and at least one type of lipid molecule.

Further features and advantages of certain embodiments of the present disclosure will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which.

DETAILED DESCRIPTION

In the following description of various examples of therapeutic cancer vaccines and related methods of treatment of the disclosure, reference is made to the accompanying drawings, which form a part hereof, and in which are shown by way of illustration various example structures and environments in which aspects of the disclosure may be practiced. It is to be understood that other structures and environments may be utilized and that structural and functional modifications may be made from the specifically described structures and methods without departing from the scope of the present disclosure.

Figure 1:
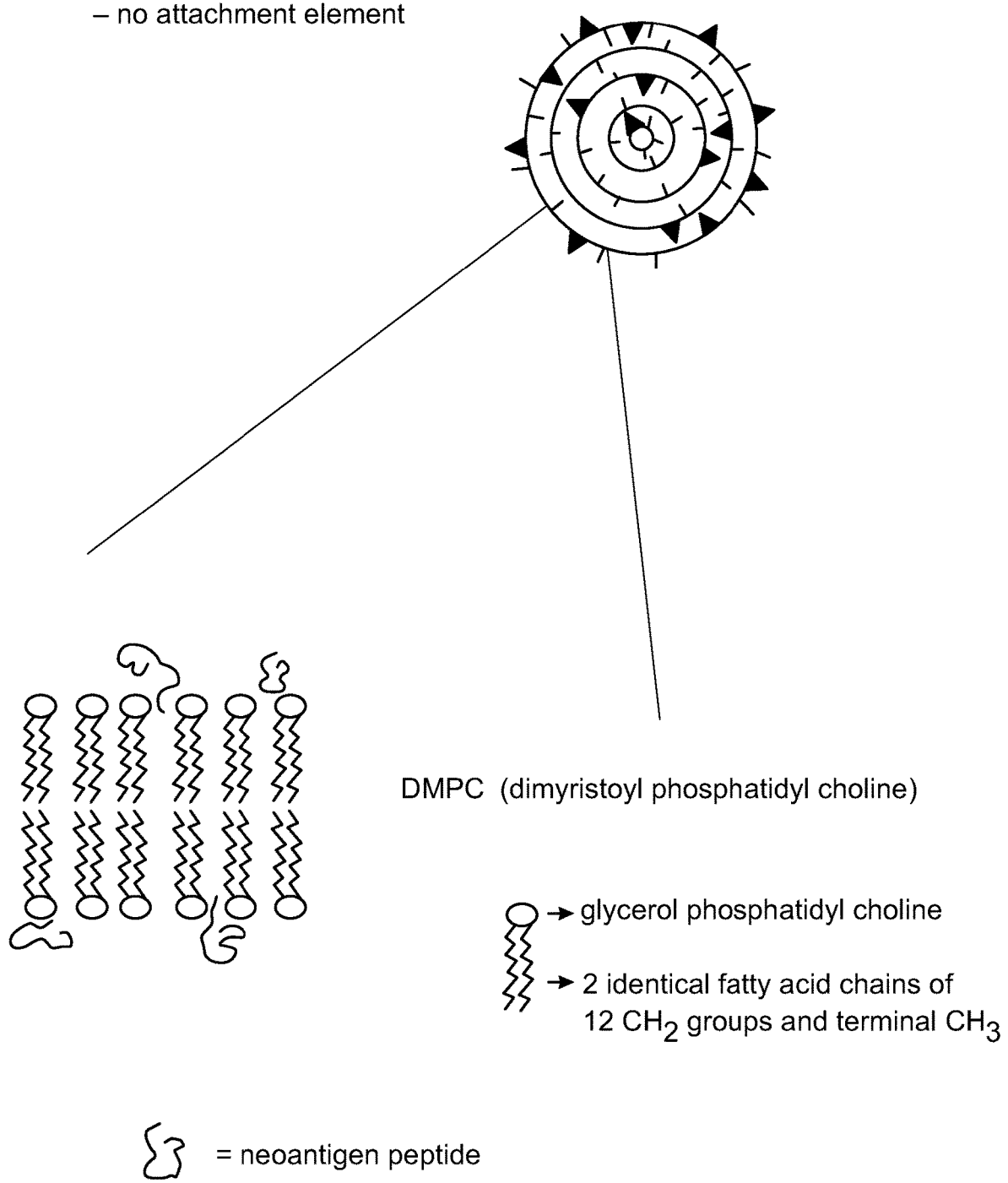
FIG. 1 schematically depicts a cancer vaccine incorporating tumor neoantigen peptides within a multilamellar liposome structure consisting of phospholipid bilayers. The expanded view of the liposome schematically depicts the structure of DMPC (dimyristoyl phosphatidy choline) composed of fatty acid chains and the glycerol phosphatidylcholine headgroup.

Aspects of the present disclosure are directed to a therapeutic cancer vaccine that includes 1) at least one neoantigen, wherein the neoantigen comprises a tumor-associated genetic mutation peptide, and wherein the tumor-associated genetic mutation peptide further includes an attachment element selected from the group consisting of a transmembrane domain, a fatty acid linker, and a tryptophan attachment element (or combinations thereof), wherein the attachment element comprises a peptide sequence of 1 to 30 amino acids; 2) at least one immunostimulant; and 3) at least one type of lipid molecule. FIG. 1 shows such a cancer vaccine that incorporates tumor-neoantigen peptides along with the immunostimulant, IL-2, in a multilamellar liposome structure consisting of phospholipid bilayers. In another exemplary embodiment of the disclosure, the therapeutic cancer vaccine includes a neoantigen that is identified by a genetic sequencing of the RNA (or DNA) contained in a hematologic tumor or a solid tumor-tissue sample obtained by needle biopsy, surgical excision, or other suitable method from one or more tumor sites of a patient. The genetic sequencing of a patient's tumor sample may be performed by techniques readily known to one skilled in the art or by using standard procedures, as described, for example, in U.S. Patent Publication No. 2011/0293637, Composition and Methods of Identifying Tumor Specific Neoantigens, incorporated herein by reference in its entirety for all purposes. After the genetic sequencing is completed, the identified peptide sequences surrounding the cancer mutation are evaluated for their potential binding affinity to the patient's Class I and Class II MHC proteins. By using techniques readily known to one skilled in the art, the neoantigen peptides with the highest binding affinity for the patient's MHC proteins are selected for use in the vaccine. In certain aspects, one or more of the identified neoantigen peptides are engineered by using automated synthetic techniques, readily known to those skilled in the art, and incorporated, with at least one immunostimulant, into a liposome as depicted in FIG. 1.

In another aspect, the vaccine includes a neoantigen that is a fusion peptide, wherein the fusion peptide comprises a plurality of different tumor-associated genetic mutations. The fusion peptide of the vaccine can be engineered to incorporate multiple peptide sequences that contain different genetic cancer mutations and are combined as one or more longer peptide sequences. Again, the different neoantigens can be combined by any technique already known to those skilled in the art. For example, peptides of up to 70 amino acids in length can be routinely synthesized by solid-phase automated peptide synthesis instruments. This would allow fusion of several MHC Class I neoantigen peptides (8-11 amino acids in length). Moreover, multiple synthetic fusion peptides of 70 amino acids in length can be chemically ligated to engineer a much longer fusion peptide. Folding and solubility may, however, be a concern as the length is increased. In one aspect, the vaccine includes a neoantigen that is selected based upon a predicted affinity for binding to the patient's MHC. As discussed above, the patient's neoantigen peptides that have been identified as having the highest binding affinity to the MHC proteins can be combined into one or more fusion peptides, or the various neoantigen peptides can be incorporated into the vaccine individually. It is believed that a synergistic or additive effect will come from having multiple different neoantigen mutation peptides, regardless of whether or not the peptides are individually incorporated into a liposome vaccine or as one fusion peptide, that will elicit a more effective immune response to the targeted cancer of the patient. As shown in FIG. 1, the vaccine includes at least one fusion peptide, together with at least one immunostimulant, into a liposome.

Figure 2:
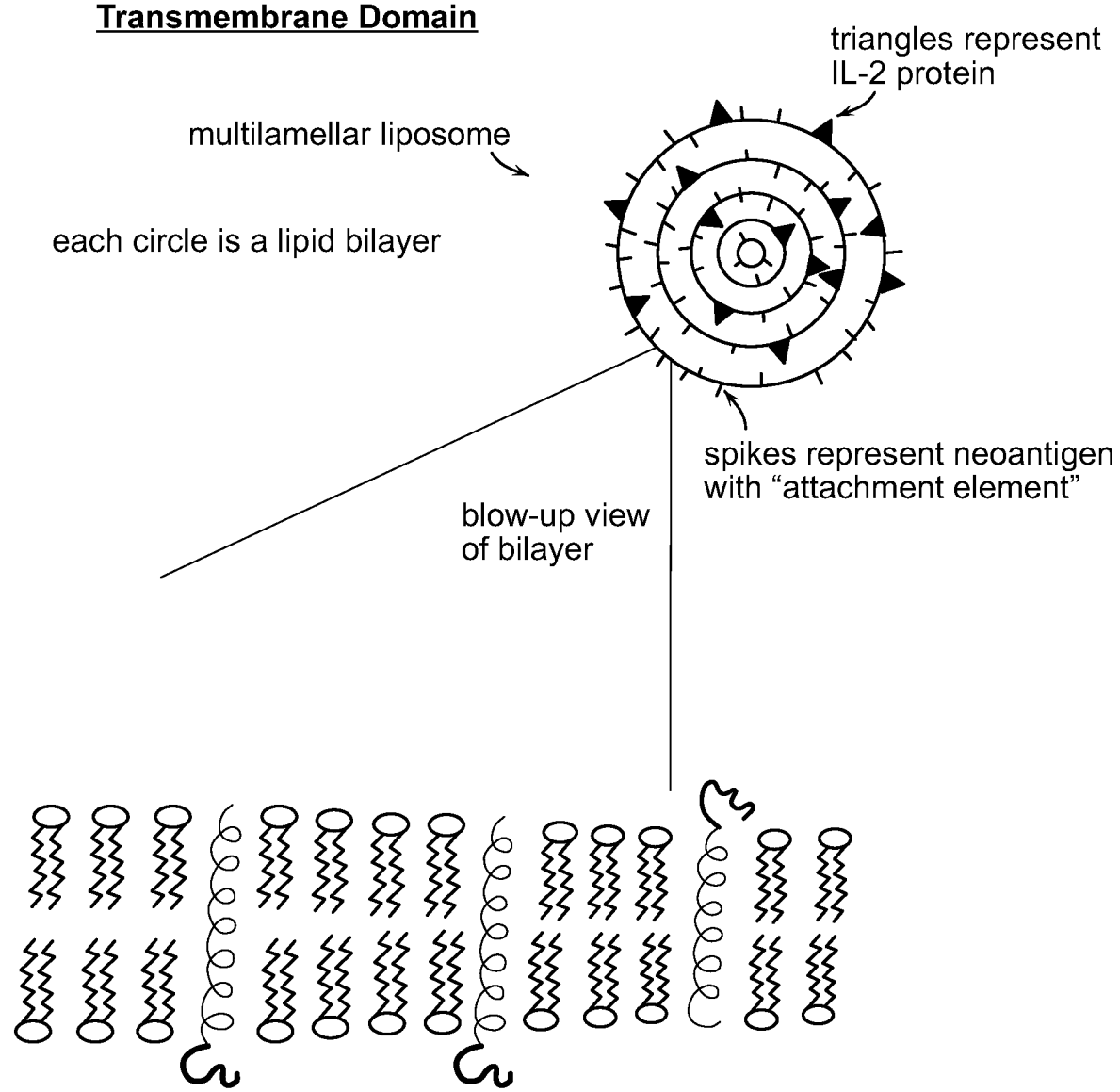
FIG. 2 schematically depicts a cancer vaccine incorporating tumor neoantigen peptides within a multilamellar liposome structure consisting of phospholipid bilayers via a transmembrane domain. The expanded view schematically depicts the transmembrane alpha helix penetrating across the entire phospholipid bilayer.

In yet another aspect, the vaccine includes a lipid molecule that is selected from the group consisting of phospholipids, glycolipids, cholesterol, and derivatives of the lipid molecules. In still yet other aspects, the lipid molecule is a saturated or an unsaturated phospholipid or glycolipid, or any combination of such molecules. In other aspects, the lipid molecule can include 1,2 dimyristoylphosphatidyl choline, 1,2 dipalmitoylphosphatidyl choline, 1,2 dimyristoylphosphatidyl glycerol, cholesterol, cholesterol hemisuccinate and other derivatives of the above. The lipid molecule further includes lipid bilayers. In certain aspects, the neoantigen is engineered to include the tumor-associated mutation peptide that also includes an attachment element, and the attachment element is a transmembrane domain attachment element, a fatty acid linker, a tryptophan attachment element, a combination thereof, or other attachment elements that integrate or anchor themselves, along with the neoantigen, into or onto the lipid bilayers as shown in FIG. 2. The transmembrane domain attachment element includes a peptide sequence of 20 to 30 amino acids. Transmembrane domains generally consist of alpha helical peptide segments that span the entire lipid bilayer and typically consist of a minimum of 20-25 amino acids. In other aspects, the transmembrane domain includes peptide sequences of 25-30, 30-35, or 35-40 amino acids. In still other aspects, the transmembrane domain includes peptide sequences of 25, 30, 35, 40, and 45 amino acids. In other aspects, the transmembrane domain includes peptide sequences of at least 20 amino acids in length. In yet other aspects, the transmembrane domain includes peptide sequences of 30 to 70 amino acids in length. In other aspects, the transmembrane domain may include additional spacer amino acids or may include charged amino acids to anchor the transmembrane domain attachment element on the opposite side of the lipid bilayer. In still other aspects, the neoantigen is engineered to include the tumor-associated mutation peptide that also includes an attachment element. Attachment elements do not generally span the entire phospholipid bilayer if the attachment element consists of 20 or less amino acids.

Other aspects of the present disclosure are directed to a therapeutic cancer vaccine that includes 1) at least one neoantigen, wherein the neoantigen includes a tumor-associated genetic mutation peptide, and wherein the tumor-associated genetic mutation peptide further includes an attachment element selected from the group consisting of a transmembrane domain, a fatty acid linker, and a tryptophan attachment element, wherein the attachment element comprises a peptide sequence of 1 to 30 amino acids; 2) at least one immunostimulant; and 3) at least one type of lipid molecule. In another aspect, the transmembrane domain attachment element is extended at its amino terminal end with at least one amino acid. The amino terminal end of the transmembrane domain will link to the neoantigen peptide and may have additional "spacer" amino acids in between. In yet another aspect, the transmembrane domain attachment element is extended at a carboxy terminal end with at least one amino acid. In yet another aspect, the transmembrane domain attachment element is: $NH^2$-TTEYQVAVAGIVFL-LISVLLLSGLTWQRRQRK-COOH (SEQ ID NO:1). According to one aspect, the peptide containing the genetic mutation is preceded during automated synthesis by a hydrophobic peptide sequence of 20 to 30 amino acids. In one aspect, the synthesized peptide includes 1-50 amino acids. In another aspect, the synthesized peptide includes 1-70 amino acids. In one aspect, the engineered peptide acts as a membrane attachment element or transmembrane anchoring element for incorporation into the lipid bilayers of the liposomes comprising the vaccine. According to one aspect, the engineered neoantigen can have the following general structure:

[$NH_2$-Neoantigen Sequence-Attachment Element-COOH]

Figure 3:
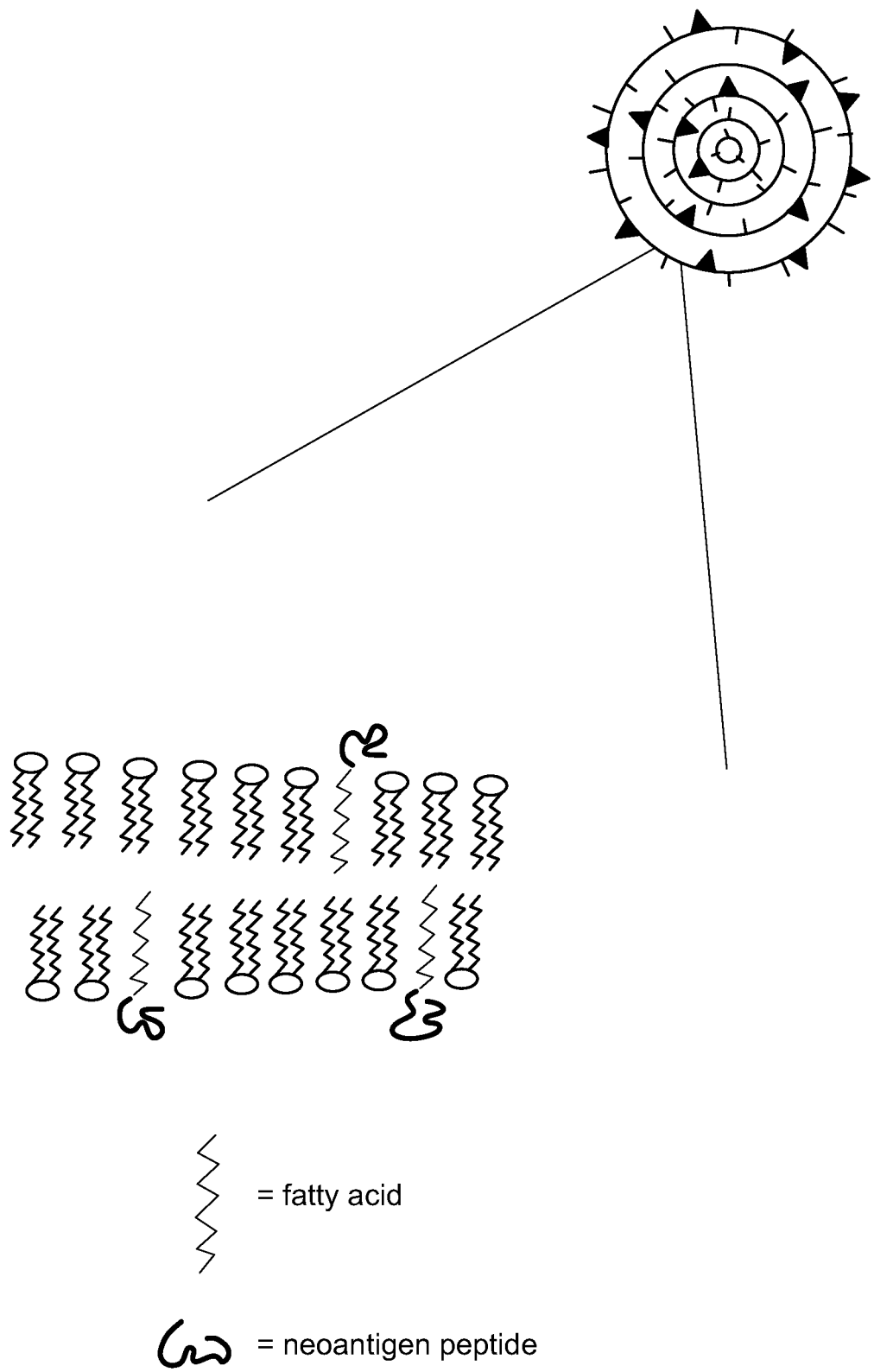
FIG. 3 schematically depicts a cancer vaccine incorporating tumor neoantigen peptides within a multilamellar liposome structure consisting of phospholipid bilayers via a fatty acid linker. The expanded view schematically depicts the fatty acid and neoantigen peptide anchored to the phospholipid bilayer.

In yet another embodiment, the vaccine includes a neoantigen that further includes a tumor-associated genetic mutation peptide, wherein the tumor-associated genetic mutation peptide further includes an attachment element, wherein the attachment element is a fatty acid linker, and the fatty acid linker is attached to the neoantigen through an epsilon amino group, and the epsilon amino group is part of a lysine residue. For example, the neoantigen peptide can be extended at its carboxy terminus with a lysine residue to which a fatty acid is attached through the lysine epsilon amino group. The fatty acid integrates with the lipid bilayers as shown in FIG. 3. It is noted that the fatty acid conjugation to the neoantigen by an epsilon amino group is a single example of chemically linking fatty acids to peptides. Accordingly, one skilled in the art would understand that there are other mechanisms to provide such a linkage. For example, peptides with extensions of one or more amino acids to the neoantigen sequence at its N or C-terminus may be conjugated to a fatty acid. Further, more than one fatty acid may be conjugated to the extension of the neoantigen sequence.

Figure 4:
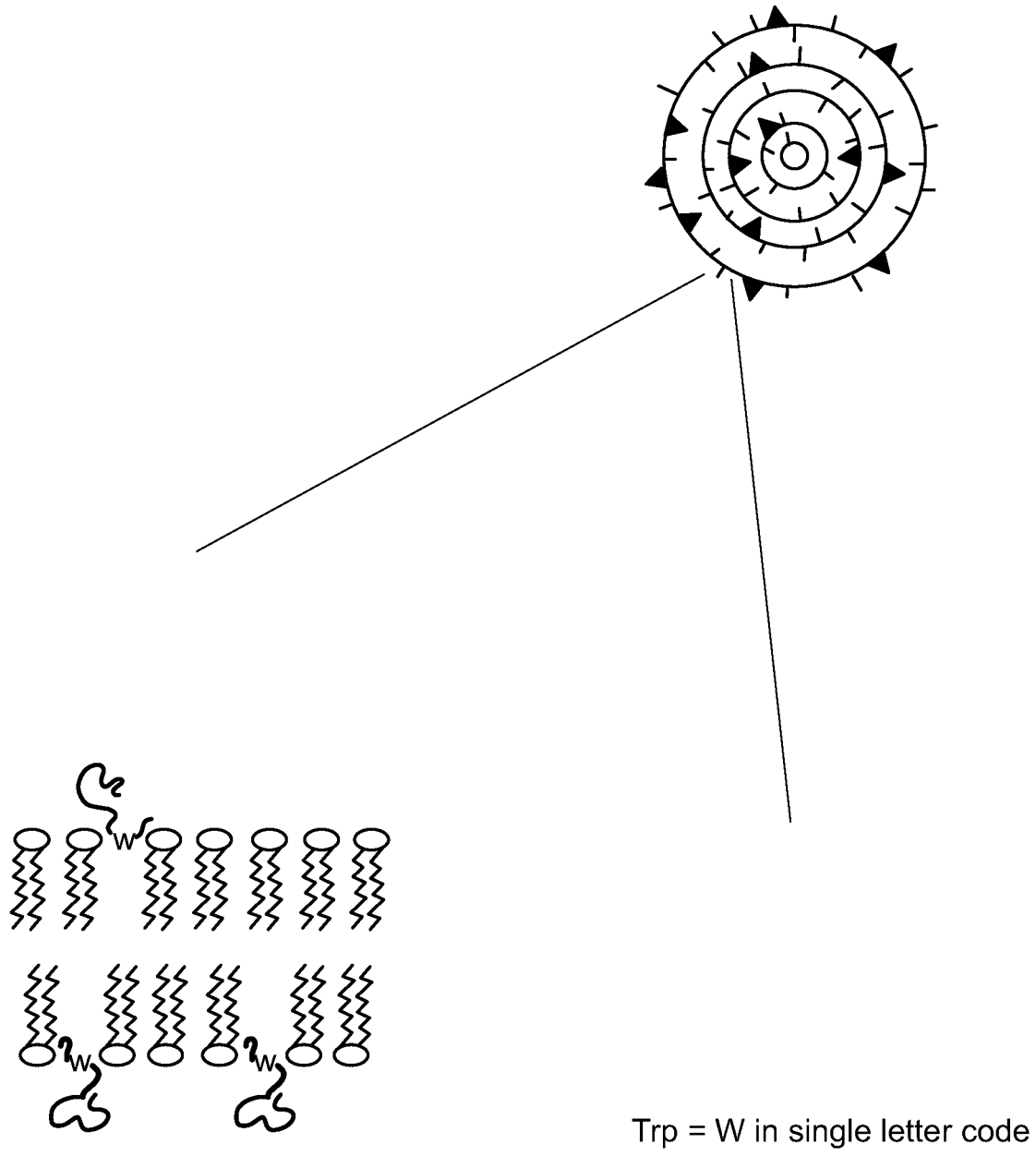
FIG. 4 schematically depicts a cancer vaccine incorporating tumor neoantigen peptides within a multilamellar liposome structure consisting of phospholipid bilayers via an attachment element comprising a tryptophan (Trp-W) attachment element. The expanded view schematically depicts the tryptophan attachment element and neoantigen peptide anchored to the phospholipid bilayer.

In another embodiment, wherein the vaccine further includes a neoantigen, wherein the neoantigen further includes a tumor-associated genetic mutation peptide, and wherein the tumor-associated genetic mutation peptide further includes an attachment element, wherein the attachment element is a tryptophan attachment element, and the tryptophan attachment element includes at least one tryptophan amino acid as shown in FIG. 4. According to one aspect, the amino acid extension contains a tryptophan, two or more tryptophans, or is entirely composed of tryptophan. In one aspect, the tryptophan attachment element is NRWIT (SEQ ID NO:2). In another aspect, the membrane attachment element is any sequence of amino acids having an affinity for lipid membranes. According to another aspect, the amino acid attachment element, or transmembrane attachment or anchoring element is added to synthesis of the neoantigen peptide at the amino and/or carboxy terminal end and/or at any position within the neoantigen peptide sequence. In another embodiment, the membrane attachment element is a synthetic polymer able to be attached during or after synthesis of the neoantigen peptide and added at the amino and/or carboxy terminal end and/or at any position within the neoantigen peptide sequence.

In yet another embodiment, the therapeutic cancer vaccine that includes 1) at least one neoantigen, wherein the neoantigen includes a tumor-associated genetic mutation peptide, and wherein the tumor-associated genetic mutation peptide further includes a transmembrane domain attachment element, wherein the transmembrane domain attachment element includes a peptide sequence of 20 to 30 amino acids; 2) at least one immunostimulant; 3) and at least one type of lipid molecule; and the vaccine further includes either 4) a second antigen that includes at least one second tumor-associated genetic mutation peptide, wherein the second tumor-associated genetic mutation peptide further includes an attachment element, wherein the attachment element is a fatty acid linker, and wherein the fatty acid linker includes one or more amino acids chemically modified to include at least one hydrophobic peptide that integrates with the lipid bilayers; or the vaccine further includes 5) a third neoantigen, wherein the third neoantigen includes a tumor-associated genetic mutation peptide, and wherein the tumor-associated genetic mutation peptide further includes an attachment element, wherein the attachment element is a tryptophan attachment element, and the tryptophan attachment element includes at least one tryptophan amino acid. In yet another embodiment, the vaccine includes at least one of both the second and the third neoantigens described above.

In another aspect, the peptide containing the genetic mutation is synthesized without altering the basic tumor neoantigen sequence, using one or more amino acids that are chemically modified with the addition of one or more hydrophobic entities known in the art to interact with and/or integrate into lipid membranes. In yet another aspect, the chemical modification consists of one or more fatty acid or phospholipid molecules to improve the integration of the peptide into the lipid bilayers of the liposomes comprising the vaccine. In another aspect, the chemical modification includes any chemical having an affinity for lipid membranes. In still another aspect, the amino and/or carboxy terminal ends of the neoantigen peptide are extended with one or more amino acids, at least one of which has a chemical modification known to interact with lipid membranes. In other aspects, the chemical modification is added after synthesis of the neoantigen peptide. In other aspects, the chemical modification is added at the same time as the synthesis of the neoantigen peptide.

In another embodiment, the present disclosure is directed to a therapeutic cancer vaccine that includes at least one neoantigen, wherein the neoantigen includes a tumor-associated genetic mutation peptide, and wherein the tumor-associated genetic mutation peptide further includes an attachment element selected from the group consisting of a transmembrane domain, a fatty acid linker, and a tryptophan attachment element, wherein the attachment element comprises a peptide sequence of 1 to 30 amino acids; at least one immunostimulant; and at least one type of lipid molecule. In one aspect, the immunostimulant includes one or more cytokines, such as interleukin 2 (IL-2), GM-CSF, M-CSF, and interferon-gamma (IFN-γ), one or more Toll-like Receptor agonists and/or adjuvants, such as monophosphoryl lipid A, lipid A, muramyl dipeptide (MDP) lipid conjugate and double stranded RNA, or one or more costimulatory membrane proteins and/or cell adhesion proteins, such CD80, CD86 and ICAM-1, or any combination of the above. In one aspect, the vaccine includes an immunostimulant that is a cytokine selected from the group consisting of interleukin 2 (IL-2), GM-CSF, M-CSF, and interferon-gamma (IFN-γ). In another aspect, the vaccine includes an immunostimulant that is a Toll-like Receptor agonist and/or adjuvant selected from the group consisting of monophosphoryl lipid A, lipid A, and muramyl dipeptide (MDP) lipid conjugate and double stranded RNA. In yet another aspect, the vaccine includes an immunostimulant that is a costimulatory membrane protein and/or cell adhesion protein selected from the group consisting of CD80, CD86, and ICAM-1.

Other aspects of the disclosure relate to a method of treating cancer in a patient by administering to the patient an effective amount of a therapeutic cancer vaccine that includes at least one neoantigen, wherein the neoantigen includes a tumor-associated genetic mutation peptide, and wherein the tumor-associated genetic mutation peptide further includes 1) an attachment element selected from the group consisting of a transmembrane domain, a fatty acid linker, and a tryptophan attachment element, wherein the attachment element comprises a peptide sequence of 1 to 30 amino acids; 2) at least one immunostimulant; 3) and at least one type of lipid molecule.

The vaccine is manufactured by aseptic techniques by any method for creating multilamellar liposomes that is readily known to one skilled in the art. For example, the vaccine can be manufactured by combining sterilized solutions of neoantigen peptides, immunostimulants, and lipids, and subjecting the combination to repeated cycles of freezing, thawing, and sonication within a sterilized reaction vessel. The vaccine can also be made by adding a sterilized solution of neoantigen peptides and a sterilized solution of immunostimulants, sequentially or simultaneously, to a sterilized solution of lipids in the form of small unilamellar vesicles, all within a sterilized reaction vessel. The reaction vessel is incubated at a prescribed temperature for a prescribed length of time during which multi-lamellar liposomes form incorporating the peptides and immunostimulants within and between the lipid bilayers. Once manufactured, the vaccine is aseptically divided into sterilized vials which are sealed and stored for use.

Other aspects of the disclosure relate to a method of cancer treatment by inducing humoral and cellular immune responses against cancer cells in a patient that includes the steps of genetically sequencing a tumor-tissue sample from a patient to identify a plurality of neoantigens present in the tumor-tissue sample, and wherein the neoantigens include tumor-associated genetic mutation peptides. At least one neoantigen is selected based upon a predicted affinity for binding to the MHC of the patient, wherein the corresponding MHC proteins on the surface of the antigen-presenting cells of the patient bind and present the neoantigens to helper and effector T cells of the patient's immune system. Resultantly, the patient's immune system then directs an effective immune response to the cancer cells in a patient. As discussed above, to identify those neoantigens that have the highest affinity for binding to the particular patient's MHC, a genetic sequencing (i.e., nucleic acid) is performed on the biopsy material to identify the full range of genetic mutations (i.e., neoantigens), present in the proteins associated with the biopsy material. Again, the genetic sequencing of a patient's cancer sample may be performed by techniques readily known to one skilled in the art or by using standard procedures, as described above.

According to one aspect, the patient is then administered a therapeutically effective amount of a vaccine that includes the neoantigen peptides identified as those with the highest binding affinity for the patient's MHC proteins. According to another aspect, the neoantigen, which includes a tumor-associated genetic mutation peptide, further includes an attachment element selected from the group consisting of a transmembrane domain, a fatty acid linker, and a tryptophan attachment element (or combinations thereof), wherein the attachment element comprises a peptide sequence of 1 to 30 amino acids; at least one immunostimulant; and at least one type of lipid molecule.

Other aspects of the disclosure relate to method of cancer treatment by inducing humoral and cellular immune responses against cancer cells in a patient that includes genetically sequencing a tumor-tissue sample from a patient to identify a plurality of neoantigens present in the tumor-tissue sample, and wherein the neoantigens comprise tumor-associated genetic mutation peptides, then selecting at least one neoantigen based upon a predicted affinity for binding to a Major Histocompatibility Complex (MHC) of the patient, wherein MHC proteins on a surface of antigen-presenting cells of the patient bind and present the neoantigens to helper and effector T cells of an immune system of the patient, wherein an immune response is directed to the cancer cells in a patient, subsequently administering to the patient a therapeutically effective amount of a vaccine that includes the neoantigen, wherein the neoantigen includes a tumor-associated genetic mutation peptide, and wherein the tumor-associated genetic mutation peptide further includes an attachment element selected from the group consisting of a transmembrane domain, a fatty acid linker, and a tryptophan attachment element, wherein the attachment element comprises a peptide sequence of 1 to 30 amino acids; at least one immunostimulant; and at least one type of lipid molecule. According to other aspects, the method of cancer treatment by inducing humoral and cellular immune responses against cancer cells in a patient may include any of the vaccines, components of the vaccines, or combinations of the vaccines described above.

According to another aspect, the method of cancer treatment by inducing humoral and cellular immune responses against cancer cells in a patient may include administering the vaccine to the patient at a prescribed dose by intradermal, subcutaneous, intramuscular, intranodal, or intra-tumoral injection, or any combination thereof. According to another aspect, the patient receives multiple vaccine injections at separate sites or the patient may receive multiple vaccine injections at the same site. According to yet another aspect, the patient receives multiple vaccinations at prescribed time intervals. According to other aspects, the time intervals may include time intervals such as every 1, 2, 3, or 4 weeks or every 2 to 4 weeks.

An effective therapeutic vaccine and related method of treatment by inducing humoral and cellular immune responses against malignant cells is described in this disclosure. The vaccine comprises a delivery system that incorporates at least one peptide whose sequence encompasses a patient-specific genetic mutation associated with malignancy (neoantigen), at least one immunostimulant, and at least one type of lipid molecule. Such a combination provides a novel and more potent vaccine formulation for treating cancer. The disclosed vaccine and related method provide a synergistic effect that induces a more effective immune response, uniquely tailored for an individual patient's tumor cells, directed against the patient's malignant cells.

As used herein, the terms "protein" and "polypeptide" and "peptide" are used interchangeably herein to designate a series of amino acid residues, connected to each other by peptide bonds between the alpha-amino and carboxy groups of adjacent residues. The terms "protein," "peptide," and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "peptide" are used interchangeably herein when referring to a gene product and fragments thereof. Thus, exemplary polypeptides, peptides, or proteins include gene products, naturally occurring proteins, homologs, orthologs, paralogs, fragments and other equivalents, variants, fragments, and analogs of the foregoing.

An "antigen" is a substance that upon introduction into a vertebrate animal stimulates the production of antibodies or cell-mediated immune responses. A "tumor-associated antigen" is a molecule produced by or associated with malignant cells, but is not normally expressed, or expressed at very low levels, by a non-malignant cell. A "neoantigen" is class of tumor antigens that arises from tumor-specific mutations in an expressed protein.

Proteins or molecules of the "major histocompatibility complex (MHC)" are proteins capable of binding peptides that result from the proteolytic cleavage of protein antigens and representing potential T-cell epitopes, transporting them to the cell surface and presenting them there to specific cells, in particular cytotoxic T-lymphocytes or T-helper cells. The MHC of an individual's genome comprises the genetic region whose gene products expressed on the cell surface are important for binding and presenting endogenous and/or foreign antigens for regulating immune response. The major histocompatibility complex is classified into two gene groups coding for different proteins, namely molecules of MHC class I and molecules of MHC class II. The molecules of the two MHC classes are specialized for different antigen sources. The molecules of MHC class I present endogenously synthesized antigens, for example viral proteins and tumor antigens.

A "lipid" is any of a group of biochemicals which is variably soluble in organic solvents, such as alcohol. Examples of lipids include phospholipids, fats, waxes, and sterols, such as cholesterol. A "liposome" is a microscopic vesicle that consists of one or more lipid bilayers surrounding an aqueous compartment.

A "vaccine" is a material that is administered to a vertebrate host to immunize the host against the same material. Typically, a vaccine comprises material associated with a disease state, such as viral infection, bacterial infection, and various malignancies. A "therapeutic vaccine" is a vaccine administered to a vertebrate host which already has the disease being targeted and is designed to induce an immune response that causes disease regression, delayed disease progression, prolonged disease-free survival and/or overall survival.

An "immunostimulant" is any substance that stimulates the immune system by inducing activation or increasing activity of any of the immune system's components.

An "amino acid sequence" may be determined directly for a protein or peptide, or inferred from the corresponding nucleic acid sequence.

A "nucleic acid" or "nucleic acid sequence" may be any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

Definitions of common terms in cell biology and molecular biology can be found in The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present disclosure is performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); and Current Protocols in Protein Science (CPPS) (John E. Coligan, et. al., ed., John Wiley and Sons, Inc.), which are all incorporated by reference herein in their entireties.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The following examples are set forth as being representative of the present disclosure. These examples are not to be construed as limiting the scope of the present disclosure as these and other equivalent embodiments will be apparent in view of the present disclosure, figures and accompanying claims.

EXAMPLE I

Transmembrane Domain Attachment Element

Using a solid phase automated peptide synthesizer, manufacture the peptide corresponding to the neoantigen amino acid sequence together with a carboxy-terminal extension corresponding to a transmembrane domain (TMD). Begin the synthesis at the carboxy-terminal end of the TMD and proceed to the amino terminus, followed by the sequence corresponding to the neoantigen peptide. An example of a transmembrane domain is:

```
Example Transmembrane Domain
NH2-Neoantigen Sequence-
                                        (SEQ ID NO: 1)
TTEYQVAVAGIVFLLISVLLLSGLTWQRRQRK-COOH
```

When synthesis is complete, chemically remove the peptide from the solid phase resin and lyopholize. Reconstitute the peptide at a concentration of 1 to 10 mg/mL in an appropriate buffer, such as 0.9% saline containing 0.5% diheptanoyl phosphatidylcholine, DHPC.

Prepare small unilamellar vesicles (SUV) of a phospholipid, such as dimyristoyl phosphatidylcholine (DMPC), or a mixture of lipids (phospholipids, cholesterol, etc.) by high pressure homogenization. Set aside at 37° C. until used.

Prepare a solution of immune stimulant or mixture of immune stimulants in 0.9% saline. For this example, the immune stimulant is recombinant human Interleukin 2 (IL-2) and the concentration of the solution is $40 \times 10^6$ IU/mL.

The final product is assembled under aseptic conditions in an ISO 5 Biological Safety Cabinet (BCC), preferably within an ISO 7 Clean Room. For this example, the reaction vessel consists of a 20 mL glass vial with a magnetic stir bar, both of which have been sterilized by dry heat sterilization. The reaction vessel is placed on a magnetic stirrer containing a heating element and maintained at 25° C. during the preparation of the vaccine. During the addition of the components to the reaction vessel, the liquid contents within the vessel are mixed continuously using the stir bar. Using a sterile disposable polypropylene syringe and a sterile 0.2 µm filter, 6.4 mL of the DMPC SUV is filtered directly into the glass reactor vessel. Using a separate syringe and 0.2 µm filter, 6.4 mL of neoantigen solution (1 to 10 mg/mL protein) is filtered into the reaction vessel. With a third syringe and 0.2 µm filter, 2.0 mL of diluted IL-2 ($80 \times 10^6$ IU total) is filtered into the reaction vessel. The volume of the reaction mixture is 14.8 mL. Once all the components have been added and mixed, the reaction vessel is sealed with a sterile rubber septum and metal ring crimp. It is then transferred to an incubator at 19±2° C. for 2 to 24 hrs.

After the incubation period is complete, the reaction vessel is moved to an ISO 5 BSC where it is opened and 5.2 mL of sterile 0.9% saline is added to bring the total volume to 20 mL. The contents are mixed briefly on a magnetic stirrer to assure homogeneity and the product is then subdivided for final use.

Measure incorporation of the neoantigen-TMD peptide and the immune stimulant IL-2 active components as follows:

For the Total content of the component in the final vaccine product, dissolve the liposomes by combining a sample of vaccine with an equal volume of 5% (w/v) of an appropriate detergent, such as Igepal CA-630. Measure the content of IL-2 using a commercial capture ELISA assay. Measure the content of neoantigen(s)-TMD by running a sample on reverse phase HPLC and quantitating by using standard curves derived with the individual purified neoantigen-TMD peptides. For the Free content of the components, dilute a sample of vaccine with an equal volume of 0.9% saline and centrifuge at 20,000 rcf for 15 min at 4° C. Remove the supernatant containing non-incorporated material. Assay for Free IL-2 using the commercial capture ELISA assay and for Free neoantigen(s) using reverse phase HPLC quantitated by standard curves.

EXAMPLE II

Tryptophan Attachment Element

Using a solid phase automated peptide synthesizer, manufacture peptide corresponding to the neoantigen amino acid sequence together with a carboxy-terminal attachment element containing one or more tryptophans (Trp; W). Begin the synthesis at the carboxy-terminal end of the attachment element and proceed to the amino terminus, followed by the sequence corresponding to the neoantigen peptide. An example of a TRP-containing attachment element is:

```
Example Tryptophan Attachment Element
                                         (SEQ ID NO: 2)
NH2-Neoantigen Sequence-NRWIT-COOH
```

When synthesis is complete, chemically remove the peptide from the solid phase resin and lyopholize. Reconstitute the peptide at a concentration of 1 to 10 mg/mL in an appropriate buffer, such as 0.9% saline.

filter, 6.4 mL of neoantigen solution (1 to 10 mg/mL protein) is filtered into the reaction vessel. With a third syringe and 0.2 μm filter, 2.0 mL of diluted IL-2 ($80 \times 10^6$ IU total) is filtered into the reaction vessel. The volume of the reaction mixture is 14.8 mL. Once all components have been added and mixed, the reaction vessel is sealed with a sterile rubber septum and metal ring crimp. It is then transferred to an incubator at 19±2° C. for 2 to 24 hrs.

After the incubation period is complete, the reaction vessel is moved to an ISO 5 BSC where it is opened and 5.2 mL of sterile 0.9% saline is added to bring the total volume to 20 mL. The contents are mixed briefly on a magnetic stirrer to assure homogeneity and the product is then subdivided for final use. Measure the incorporation of the neoantigen peptide(s) and IL-2 as in Example I above.

```
                            SEQUENCE LISTING

<160> NUMBER OF SEQ ID NOS: 2

<210> SEQ ID NO 1
<211> LENGTH: 32
<212> TYPE: PRT
<213> ORGANISM: Artificial
<220> FEATURE:
<223> OTHER INFORMATION: transmembrane domain attachment element

<400> SEQUENCE: 1

Thr Thr Glu Tyr Gln Val Ala Val Ala Gly Ile Val Phe Leu Leu Ile
1               5                   10                  15

Ser Val Leu Leu Leu Ser Gly Leu Thr Trp Gln Arg Arg Gln Arg Lys
            20                  25                  30

<210> SEQ ID NO 2
<211> LENGTH: 5
<212> TYPE: PRT
<213> ORGANISM: Artificial
<220> FEATURE:
<223> OTHER INFORMATION: tryptophan attachment element

<400> SEQUENCE: 2

Asn Arg Trp Ile Thr
1               5
```

Prepare small unilamellar vesicles (SUV) of a phospholipid, such as dimyristoyl phosphatidylcholine (DMPC), or a mixture of lipids (phospholipids, cholesterol, etc.) by high pressure homogenization. Set aside at 37° C. until used.

Prepare a solution immune stimulant or mixture of immune stimulants in 0.9% saline. For this example, the immune stimulant is recombinant human Interleukin 2 (IL-2) and the concentration of the solution is $40 \times 10^6$ IU/mL.

The final product is assembled under aseptic conditions in an ISO 5 Biological Safety Cabinet (BCC), preferably within an ISO 7 Clean Room. For this example, the reaction vessel consists of a 20 mL glass vial with a magnetic stir bar, both of which have been sterilized by dry heat sterilization. The reaction vessel is placed on a magnetic stirrer containing a heating element and maintained at 25° C. during the preparation of the vaccine. During the addition of the components to the reaction vessel, the liquid contents within the vessel are mixed continuously using the stir bar. Using a sterile disposable polypropylene syringe and a sterile 0.2 μm filter, 6.4 mL of the DMPC SUV is filtered directly into the glass reactor vessel. Using a separate syringe and 0.2 μm

The invention claimed is:

1. A therapeutic cancer vaccine comprising:
   at least one neoantigen, wherein the neoantigen comprises a tumor-associated genetic mutation peptide, and wherein the tumor-associated genetic mutation peptide further includes a tryptophan attachment element consisting of NRWIT (SEQ ID NO:2);
   at least one immunostimulant; and
   at least one type of lipid molecule.

2. The vaccine of claim 1, wherein the neoantigen is identified by a genetic sequencing of RNA or DNA contained in a hematologic tumor or a tumor-tissue sample obtained by needle biopsy or surgical excision from one or more tumor sites of a patient.

3. The vaccine of claim 1, wherein the neoantigen is a fusion peptide, wherein the fusion peptide comprises a plurality of different tumor-associated genetic mutations.

4. The vaccine of claim 1, wherein the lipid molecule is a phospholipid.

5. The vaccine of claim 1, wherein the lipid molecule comprises lipid bilayers, and wherein the attachment element integrates with the lipid bilayers.

6. The vaccine of claim 1, wherein the immunostimulant is a cytokine.

7. The vaccine according to claim 1, wherein the neoantigen is selected based upon a predicted affinity for binding to the patient's Major Histocompatibility Complex (MHC).

8. A method of cancer treatment by inducing humoral and cellular immune responses against cancer cells in a patient comprising administering to the patient an effective amount of a therapeutic cancer vaccine according to claim 1.

* * * * *